United States Patent
Abe et al.

[11] Patent Number: 5,824,818
[45] Date of Patent: Oct. 20, 1998

[54] PROCESS FOR PREPARING LACTATE

[75] Inventors: Takafumi Abe; Toshiyuki Gotoh; Takako Uchiyama; Hirofumi Higuchi; Yoshikazu Shima; Kazuto Ikemoto, all of Niigata, Japan

[73] Assignee: Mitsubishi Gas Chemical Company, Inc., Tokyo, Japan

[21] Appl. No.: 698,478

[22] Filed: Aug. 15, 1996

Related U.S. Application Data

[63] Continuation-in-part of Ser. No. 366,873, Dec. 30, 1994, abandoned.

[30] Foreign Application Priority Data

Feb. 21, 1994 [JP] Japan .................................. 6-022385

[51] Int. Cl.$^6$ .................................................. C07C 69/66
[52] U.S. Cl. ............................................................ 560/179
[58] Field of Search ............................................ 560/179

[56] References Cited

U.S. PATENT DOCUMENTS

| | | | |
|---|---|---|---|
| 1,682,347 | 8/1928 | Matheson et al. | 560/179 |
| 1,790,262 | 1/1931 | Christmann | 560/179 |
| 2,041,820 | 5/1936 | Crawford | 260/106 |
| 3,567,749 | 3/1971 | Neugebauer et al. | 260/468 |
| 4,983,757 | 1/1991 | Ishikawa et al. | 560/103 |
| 4,990,651 | 2/1991 | Ikarashi et al. | 560/103 |
| 5,225,594 | 7/1993 | Shima et al. | 562/599 |

FOREIGN PATENT DOCUMENTS

| | | |
|---|---|---|
| 0 342 458 | 11/1989 | European Pat. Off. |
| 0 406 676 | 1/1991 | European Pat. Off. |
| 0 487 853 | 6/1992 | European Pat. Off. |

OTHER PUBLICATIONS

Patent Abstracts of Japan, vol. 7, No. 143 (C–172) (1288) 22 Jun. 1983 of JP–A–58 055 444 (Mitsubishi Gas Kagaku K.K.), 1 Apr. 1983.

Patent Abstracts of Japan, vol. 14, No. 68 (C–0686) 8 Feb. 1990 of JP–A–01 290 653 (Mitsubishi Gas Chem. Co., Inc.) 22 Nov. 1989.

*Primary Examiner*—Paul J. Killos
*Attorney, Agent, or Firm*—Frishauf, Holtz, Goodman, Langer & Chick, P.C.

[57] ABSTRACT

A process for preparing a lactate which includes: (a) preparing lactonitrile from prussic acid and acetaldehyde, (b) hydrating the lactonitrile to form lactamide, (c) forming the desired lactate and formamide from lactamide and formate (or methanol and carbon monoxide), (d) separating and collecting components, having a lower boiling point than that of lactate from the reaction liquid in step (c), by distillation under specified conditions, and (e) dehydrating formamide from step (d) to form prussic acid and recycling the prussic acid to step (a). Heretofore, lactates had been manufactured by forming lactonitrile (cyanohydrin) from acetaldehyde and prussic acid, and then esterifying lactonitrile with a mineral acid or the like. However, in this conventional process, ammonium salts were formed as by-products in an amount equal to that of the lactate. According to the present invention, a lactate can be efficiently manufactured on a commercial scale without forming a large amount of the ammonium salts as by-products. In particular, the yield of the lactate can be increased by controlling the formation of 2-formyloxy propionate and also a dimer of a lactate.

17 Claims, No Drawings

PROCESS FOR PREPARING LACTATE

CROSS-REFERENCE TO RELATED APPLICATION

This application is a continuation-in-part application of application Ser. No. 08/366,873 filed Dec. 30, 1994, abandoned.

BACKGROUND OF THE INVENTION

1. Field of the Invention

The present invention relates to a process for preparing a lactate, and more specifically, it relates to a novel process for preparing a lactate from acetaldehyde and a formate which are starting materials. Lactates have been used in large quantities as coating materials, solvents for use in an electronic industry, materials for organic synthesis of medicines and the like, and materials for various polymers such as acrylic resins and biologically degradable polymers. Therefore, the lactates are industrially extremely important chemicals.

2. Description of the Related Art

An industrial method for preparing a lactate usually comprises synthesizing cyanohydrin from prussic acid and acetaldehyde as starting materials, hydrolyzing the same, and then esterifying.

As other techniques for preparing lactic acid, there are known a method which comprises allowing dinitrogen tetroxide to act on a terminal olefin, followed by hydrolysis; a method which comprises reacting acetaldehyde with carbon monoxide and water in the presence of a noble metal catalyst or an acidic catalyst; and a method which comprises halogenating the α-position of a carboxylic acid, followed by hydrolysis. These methods are poor in yields, utilize the limited material sources, require troublesome operations of the reactions, separation and purification, and also require the expensive catalysts. For these reasons, the above-mentioned methods are undesirable for industrial methods for preparing lactic acid on a large scale. In fact, these methods have been used to specifically produce lactic acid and its derivatives only on a small scale.

The above-mentioned conventional method which comprises the synthesis of cyanohydrin from prussic acid and acetaldehyde, its hydrolysis and esterification has been widely utilized, because of the easy reaction and a high yield. In this method, however, a large amount of ammonium salts are formed as by-products, and the treatment of these by-products adversely leads to an increase in lactate manufacturing cost.

SUMMARY OF THE INVENTION

The present inventors have previously found a process for preparing methacrylic acid from acetone and methyl formate as starting materials via acetone cyanohydrin without forming the by-products of ammonium salts (Japanese Patent Application Laid-open No. 198152/1992 and U.S. Pat. No. 5,225,594).

The present inventors have further researched, and as a result, it has been found that a lactate can efficiently be prepared by using acetaldehyde in place of acetone as a starting material in the above-mentioned process. The present inventors carried out further research, and found that when the separation and collection of components having a lower boiling point than that of lactate from the reaction liquid, which is obtained by a reaction step of forming the lactate and formamide, are carried out by distillation at a normal pressure or higher, the temperature at the bottom of the distillation column tends to become high to produce a formate 2-formyloxy propionate (a formic acid ester of a lactatic acid ester), lowering the yield of a lactate. Since the boiling point of 2-formyloxy propionate is nearly equal to that of a lactate, an expensive distillation column having a high separation efficiency is necessary to separate 2-formyloxy propionate.

It can be assumed that 2-formyloxy propionate is produced by the following chemical reaction: $CH_3CH(OH)COOR^1 + HCOOR^2 \rightarrow HCOOCH(CH_3)COOR^1 + R^2OH$. If a distillation is carried out at a reduced pressure so as to avoid the production of 2-formyloxy propionate, an expensive refrigerant apparatus is needed to catch and collect the components having a lower boiling point than that of lactate. The present invention has been completed on the basis of this knowledge. That is, the object of the present invention is to solve the above-mentioned problem, and such object can be achieved by a process for preparing a lactate without producing 2-formyloxy propionate, by maintaining the bottom of the distillation column at a low temperature, without using an expensive refrigerant apparatus.

That is to say, according to the present invention, there is provided a process for preparing a lactate represented by the general formula $CH_3CH(OH)COOR$ (R is an alkyl group having 1 to 8 carbon atoms) which comprises (1) a step of preparing lactonitrile from prussic acid and acetaldehyde, (2) a step of hydrating lactonitrile obtained in the previous step to form lactamide, (3) a step of forming the lactate represented by the general formula $CH_3CH(OH)COOR$ (R is as defined above) and formamide from lactamide obtained in the previous step and a formate represented by the general formula HCOOR (R is as defined above), (4) a step of separating and collecting components, having a lower boiling point than that of lactate from the reaction liquid obtained in the previous step, by distillation under the distillation condition that M is 16 or less, M being defined as follows: (retention time of liquid in the bottom of the distillation column) (hr.) multiplied by (temperature at the bottom of the distillation column minus 126) (°C.), and (5) a step of dehydrating formamide separated from the product obtained in the previous step to form prussic acid and recycling the same.

The process of the present invention can be achieved via the formation of lactonitrile, but according to this process, on the whole, the lactate can eventually be prepared from acetaldehyde and the formate as the starting materials. Hence, the process of the present invention is characterized by involving no formation of ammonium salts as by-products in contrast to a conventional technique. Further, according to the present invention, not only the formation of 2-formyloxy propionate can be avoided, but also the formation of a dimer of a lactate (lactoyl lactate) can be avoided, by lowering the temperature of the bottom of distillation column, which leads to increasing the yield of a lactate.

DESCRIPTION OF THE PREFERRED EMBODIMENTS

Next, a process of the present invention will be described in detail.

In the process of the present invention, acetaldehyde obtained by any method can be applied. In general, acetaldehyde has been utilized as a solvent or a material of various chemicals, and it has industrially been manufactured from ethylene in large quantities at a low cost by oxidation. In the present invention, acetaldehyde manufactured in this manner can usually be employed.

On the other hand, of formates for use in the process of the present invention, methyl formate obtained by any method can be used, but in general, there can be applied methyl formate manufactured on an industrial scale by a carbonylation method or a dehydrogenation method from methanol as a material, which has been produced in an extremely large amount at an extremely low cost. Furthermore, another formate, i.e., a formate (e.g., ethyl formate or propyl formate) represented by the general formula HCOOR' (wherein R' is an alkyl group having 2 to 8 carbon atoms) can easily be manufactured by ester interexchange between methyl formate and an alcohol represented by the general formula R'OH (R' is as defined above), or the like.

In the present invention, the manufacture of lactonitrile by the reaction of prussic acid and acetaldehyde has been carried out by a known technique, and it can easily be achieved at a low temperature of about 10° C. in the presence of a basic catalyst such as an alkaline metal hydroxide, ammonia or an amine.

Lactamide in the present invention can be prepared by a catalytic reaction (a hydration reaction) of a mixture of lactonitrile and water in the presence of a catalyst. As this catalyst, applicable is a catalyst effective for the hydration reaction of a nitrile. A strong acid such as sulfuric acid can also be used, but the employment of a metallic catalyst or a metal oxide catalyst is preferable from the viewpoints of handling and economy. Concretely, manganese, copper, nickel, or its oxide is effective, and manganese is particularly preferable.

No particular restriction is put on a feed weight ratio of lactonitrile to water, and it can be suitably selected in compliance with given situations. Nevertheless, the feed weight ratio is in the proper range of 10:90 to 90:10. In this system, acetaldehyde which is the material of lactonitrile, an alcohol or a ketone such as acetone can also be allowed to coexist as a solvent.

In the case that manganese oxide is used as the catalyst, the reaction temperature is preferably in the range of 10° to 150° C., more preferably 20° to 100° C. The reaction time is preferably in the range of 0.3 to 6 hours, more preferably 0.5 to 3 hours. The reaction can be accomplished by either system of a batch system and a continuous system.

In the present invention, the production of a lactate and formamide by the reaction of lactamide and the formate can be carried out by heating a mixture of lactamide and the formate in the absence of a catalyst, but it is effective to do the reaction in the presence of a solvent and a catalyst. When the employment of methyl formate is acceptable as the formate, methyl formate may be replaced with methanol and carbon monoxide.

This reaction is an equilibrium reaction, and the yield of the lactate depends upon a feed molar ratio of lactamide to the formate. The feed molar ratio of formate/lactamide is preferably in the range of 1 to 10, more preferably 2 to 8.

The addition of the solvent enhances the solubility of lactamide which is solid, and increases the selectivity of the reaction. The most preferable solvent is an alcohol corresponding to the formate, and a feed molar ratio of the alcohol to lactamide is preferably in the range of 1 to 10, more preferably 2 to 8.

As the catalyst for use in the above-mentioned reaction, i.e., the reaction of lactamide and the formate, alcoholates of alkaline metals, oxides of alkaline earth metals and strongly basic ion exchange resins are extremely excellent. The alcoholates of the alkaline metals can be synthesized from metals such as lithium, sodium and potassium and lower alcohols. Typical examples of the alcoholates of the alkaline metals include methylates, ethylates and butylates of sodium and potassium. Furthermore, examples of the oxides of the alkaline earth metals include magnesium oxide, calcium oxide and barium oxide.

As reaction conditions in the case that the alcoholate of the alkaline metal, the oxide of the alkaline earth metal or the strongly basic ion exchange resin is used as the catalyst, the reaction temperature is in the range of 20° to 80° C., the reaction time is in the range of 0.5 to 6 hours, and the amount of the catalyst to be used is suitably in the range of 0.001 to 0.30 mol per mol of lactamide.

The reaction product in this process can be separated and collected by a distillation, and an unreacted material is returned to a material system.

According to the present invention, the temperature of the bottom of the distillation column at a normal pressure or higher can be lowered, by adding a solvent having a low boiling point and also by increasing the concentration of the solvent in the bottom liquid of the distillation column so that the desired temperature of the bottom of the distillation column will be obtained. Solvents to be used in the present invention are not limited, if they have a low boiling point. However, a solvent used in the step (3) of forming a lactate and a formamide is preferable, an alcohol corresponding to that of a formate is more preferable.

To what degree the temperature of the bottom of the distillation column should be lowered will be affected by the retention time of liquid in the bottom of the distillation column. In general, the longer the retention time is, the more the temperature of the bottom will be lowered. According to the inventors' repeated research, it has been found that the above feature can be decided by allowing an M value, defined by the following equation, to be 16 or less. M=(retention time of liquid in the bottom of the distillation column)(hour)×(the temperature at the bottom of the distillation column–126)(°C.). Formamide which is produced together with the desired lactate is subjected to a dehydration reaction to form prussic acid. The thus formed prussic acid is recovered and returned to the cyanohydrin preparation step and then reused.

According to the present invention, each step proceeds in a very high yield, and the lactate can eventually be prepared in a high yield from acetaldehyde and the formate as starting materials. In addition, the formation of inconvenient by-products such as ammonium salts in a conventional method does not take place at all, and therefore it is fair to say that the present invention has an industrially extremely high value. In particular, undesirable formation of 2-formyloxy propionate and a dimer of a lactate (lactoyl lactate) can be easily avoided.

Next, the present invention will be described in more detail with reference to examples, but the scope of the present invention should not be limited to these examples.

EXAMPLE 1

(Synthesis of Methyl Lactate)

Step (1): (Synthesis of lactonitrile from prussic acid and acetaldehyde)

In a 500-ml flask equipped with a stirrer, a thermometer, a reflux condenser and a dropping funnel were placed 88.1 g of acetaldehyde and 1 ml of a 1N aqueous sodium hydroxide solution, and 59.4 g of prussic acid was added dropwise thereto while the temperature in the flask was maintained at 10° C. After the addition of prussic acid, the solution was maintained at 20° C. for 2 hours to complete the reaction. Next, 50% sulfuric acid was added thereto, thereby adjusting the pH of the produced solution to 3.

The flask was connected to a system under reduced pressure, and unreacted prussic acid was removed from the system, so that 142 g of lactonitrile was obtained as a residue. In the prussic acid fraction removed from the system, any lactonitrile was not detected.

The purity of the thus obtained lactonitrile was 98.8%, and the yield of lactonitrile based on acetaldehyde was 98.7%.

Step (2): (Synthesis of lactamide by hydration of lactonitrile)

Preparation of Catalyst

In a 1-liter flask equipped with a stirrer, a reflux condenser and a thermometer were placed 63.2 g of potassium permanganate and 500 g of water, followed by heating to 70° C. and stirring. Next, 240 g of an aqueous solution containing 96.2 g of dissolved manganese sulfate and 40 g of 15% sulfuric acid were added to the solution, and reaction was then carried out at 70° C. for 3 hours.

After the contents were cooled, the resulting precipitate was collected by suction filtration, and then washed with 2.4 l of water. Next, the precipitate cake was dried at 60° C. one whole day and night to obtain 74 g of active manganese dioxide. The thus obtained manganese dioxide would be used as a catalyst.

Hydration Reaction

In a 1-liter flask equipped with a stirrer, a reflux condenser and a thermometer were placed 121 g of lactonitrile obtained in the above-mentioned step (1), 350 g of water and 60 g of manganese dioxide in turn, and the resulting mixture was then heated and stirred at 60° C. for 5 hours to carry out reaction.

After the produced solution was cooled on ice, the catalyst was separated by suction filtration. The resulting filtrate was subjected to gas chromatography analysis, and as a result, it was apparent that the conversion of lactonitrile was 99.5% and the yield of lactamide was 97.5%.

This filtrate was concentrated to dryness under reduced pressure, thereby obtaining 148 g of lactamide having a purity of 99.5% or more as a main component.

Step (3): (Synthesis of methyl lactate and formamide from lactamide and methyl formate)

A stainless reactor with an inner-diameter of 15 mm and a length of 350 mm was filled with a catalyst comprising 50 ml of an OH-type strongly basic anionic ion exchange resin (Amberite 900, a product of Rohm & Hass Co.), previously treated with 1N-NaOH aqueous solution. The catalyst zone was heated at 50° C. by flowing hot water into a jacket attached to the reactor. Then, 16.6 g/hr. of lactamide obtained in the step (2), methyl formate and methanol (molar ratio: 1:2:3) were supplied into the catalyst zone to carry out the reaction. A reaction liquid was sampled over an hour, after 20 hours from the start of the reaction to carry out gas chromatography analysis. As a result, it was apparent that the conversion of lactamide was 60.9% and the selectivity for methyl lactate and the selectivity for formamide based on lactamide was 99.2% and 99.0%, respectively.

Next, the following distillation at a normal pressure with respect to the reaction liquid obtained above was conducted. The reaction liquid was supplied at a flow rate of 200 g/hr. into the middle stage of a distillation tower, which consists of 2 columns in series (each having a 30 mm diameter and a 300 mm length) filled with McMahon packing and having a jacketed container with inner volume of about 50 ml at the bottom thereof.

The bottom of the distillation column was heated and maintained at a prescribed temperature, by drawing out methyl formate and methanol at a recycling ratio of 0.5, from the top of the distillation column and by drawing out the bottom liquid containing methyl lactate from the bottom of the distillation column. The concentration for a formate of methyl-2-formyloxy propionate contained in the bottom liquid at each temperature of the bottom of the distillation column are shown in the following Table 1.

TABLE 1

| Methanol Concentration (wt. %) | Temperature of Bottom of Column (°C.) | Retention Time (hr.) | Methyl-2-Formyloxy Propionate Concentration in Bottom Liquid (wt. %) | M-value |
|---|---|---|---|---|
| 5.0 | 135 | 0.58 | 0.03 *(0.06) | 5.2 |
| 2.6 | 152 | 0.59 | 0.03 *(0.06) | 15.3 |
| 2.0 | 158 | 0.59 | 0.78 *(1.59) | 18.9 |
| trace | 165 | 0.60 | 1.71 *(3.42) | 23.4 |

NOTE: *indicates a molar yield (%) of methyl-2-formyloxy propionate based on the methyl lactate supplied into the distillation column. --.

Step (4): (Preparation of prussic acid by dehydration of formamide)

Preparation of Catalyst 0.88 g of sodium carbonate dissolved in 30 g of water was added to 51.5 g of manganese carbonate, followed by kneading for 1 hour. Afterward, the mixture was dried at 110° C. for 15 hours, calcined in a 10% hydrogen-nitrogen gas stream at 450° C. for 5 hours, and then ground to obtain 30 g of a catalyst having a uniform size of 10 to 20 mesh.

Reaction

A quartz reaction tube having a size of 10 mm (internal diameter)×300 mm (length) and equipped with a thermometer sheath was filled with 3.0 g of manganese oxide obtained in the above-mentioned manner, and it was then heated so that the temperature of the lower portion of the resulting catalyst layer might be maintained at 400° C. Furthermore, the reaction tube was filled with quartz Raschig rings having a size of 3 mm (diameter)×3 mm (length) as thick as 15 cm on the catalyst layer, and it was then heated up to 100° to 400° C. to form a formamide evaporating section.

While the pressure in the reaction tube was maintained at a vacuum degree of 100 mmHg, formamide obtained in the above-mentioned step (3) and air were introduced into the system through the top of the reaction tube at feed rates of 10 g/hour and 240 ml/hour, respectively.

Five hours after the start of the reaction, the resulting reaction gas was sampled for 1 hour. Prussic acid collected by allowing water and an aqueous NaOH solution to absorb the same was determined by a silver nitrate titration. In addition, ammonia dissolved in water was determined by ion chromatography, and unreacted formamide was done by gas chromatography.

As a result, it was apparent that the conversion of formamide was 99.5%, the selectivity for prussic acid was 95.2%, and the yield of ammonia was 4.3%.

EXAMPLE 2

Reactions were carried out by the same procedure as in Example 1 except that methyl formate as a starting material was replaced with ethyl formate. As a result, it was apparent that the conversion of lactamide was 86.1%, the selectivity for ethyl lactate and the selectivity for formamide based on lactamide was 99.8% and 98.4%, respectively.

EXAMPLE 3

The same procedure as in Example was carried out except that in the step (3) of Example 1, 180 g of methyl formate and 96 g of methanol were replaced with 200 g of methanol, and carbon monoxide was introduced at 40 atm, followed by heating and stirring to perform reaction. When the temperature in an autoclave had reached 60° C., carbon monoxide was fed so that reaction pressure might be maintained at 40 atm, and the reaction was continued for 3 hours.

Afterward, the temperature in the autoclave was cooled to 10° C., and the internal pressure was slowly lowered to atmospheric pressure. Afterward, the resulting product was taken out, and then subjected to gas chromatography. As a result, it was apparent that the conversion of lactamide was 81.7%, the selectivity for methyl lactate and the selectivity for formamide based on lactamide was 95.9% and 94.8%, respectively.

EXAMPLE 4

The same procedure as in Example 1 was carried out, except that the supply of the reaction liquid was 100 g/hr. in the distillation process of Step (4). The results obtained are shown in Table 2.

TABLE 2

| Methanol Concentration (wt. %) | Temperature of Bottom of Column (°C.) | Retention Time (hr.) | Methyl-2-Formyloxy Propionate Concentration in Bottom Liquid (wt. %) | M-value |
|---|---|---|---|---|
| 9.1 | 121 | 1.1 | 0.02 *(0.04) | −5.5 |
| 5.0 | 135 | 1.2 | 0.03 *(0.06) | 10.8 |
| 3.5 | 148 | 1.2 | 1.35 *(2.7 ) | 26.4 |
| 2.0 | 158 | 1.2 | 2.04 *(4.16) | 38.4 |

NOTE: *shows the same as in Table 1.--.

What is claimed is:

1. A process for preparing a lactate represented by the formula CH₃CH(OH)COOR, wherein R is an alkyl group having 1 to 8 carbon atoms, which comprises:
   (a) preparing lactonitrile from prussic acid and acetaldehyde;
   (b) hydrating the lactonitrile obtained from step (a) to form lactamide,
   (c) forming a lactate represented by the formula CH₃CH(OH)COOR, wherein R is as defined above, and formamide by reacting the lactamide obtained in step (b) with a formate represented by the formula HCOOR, wherein R is as defined above,
   (d) separating and collecting components having a lower boiling point than that of the lactate from a reaction liquid obtained in step (c) by distillation under distillation conditions that a value M is 16 or less, M being defined as a retention time of liquid in the bottom of a distillation column (hours) multiplied by the temperature at the bottom of the distillation column minus 126 (°C.), and optionally recovering the lactate, and
   (e) dehydrating formamide separated from the resultant product in step (d) to form prussic acid, recycling the prussic acid to step (a).

2. The process for preparing a lactate according to claim 1 wherein the formate used in the step (c) is methyl formate.

3. The process for preparing a lactate according to claim 1 wherein the step (a) is carried out in the presence of a basic catalyst.

4. The process for preparing a lactate according to claim 1 wherein the step (b) is carried out in the presence of a catalyst selected from the group consisting of manganese, copper, nickel, manganese oxide, copper oxide and nickel oxide.

5. The process for preparing a lactate according to claim 1 wherein the step (c) is carried out in the presence of a catalyst comprising an alcoholate of an alkaline metal, an oxide of an alkaline earth metal or a strongly basic ion exchange resin.

6. The process for preparing a lactate according to claim 1 wherein the step (a) is carried out in the presence of a basic catalyst, the step (b) is carried out in the presence of a catalyst selected from the group consisting of manganese, copper, nickel, manganese oxide, copper oxide and nickel oxide, and the step (c) is carried out in the presence of a catalyst selected from the group consisting of an alcoholate of an alkaline metal, an oxide of an alkaline earth metal and a strongly basic ion exchange resin.

7. The process for preparing a lactate according to claim 1 wherein step (a) is carried out at a temperature of about 10° C.

8. The process for preparing a lactate according to claim 1 wherein in step (b), water is added in an amount such that a feed weight ratio of the lactonitrile to water is 10:90 to 90:10.

9. The process for preparing a lactate according to claim 4 wherein the catalyst is manganese oxide and step (b) is carried out at a temperature of 10° to 150° C. for a reaction time of 0.3 to 6 hours.

10. The process for preparing a lactate according to claim 9 wherein step (b) is carried out at a temperature of 20° to 100° C. and for a reaction time of 0.5 to 3 hours.

11. The process for preparing a lactate according to claim 1 wherein step (c) is carried out with a molar feed ratio of the formate to the lactamide of 1 to 10 in the presence of a solvent, said solvent being an alcohol with a molar feed ratio of the alcohol to the lactamide of 1 to 10.

12. The process for preparing a lactate according to claim 11 wherein the molar feed ratio of the formate to the lactamide is 2 to 8 and the molar feed ratio of the alcohol to the lactamide is 2 to 8.

13. The process for preparing a lactate according to claim 12 wherein step (c) is carried out in the presence of a catalyst selected from the group consisting of (i) an alcoholate of an alkali metal selected from the group consisting of lithium, sodium and potassium, wherein said alcoholate is selected from the group consisting of a methylate, an ethylate and a butylate; (ii) an oxide of an alkaline earth metal selected from the group consisting of magnesium oxide, calcium oxide and barium oxide; and (iii) a strongly basic ion exchange resin.

14. The process for preparing a lactate according to claim 13 wherein step (c) is carried out at a temperature of 20° to 80° C., at a reaction time of 0.5 to 6 hours and the catalyst being in an amount of 0.001 to 0.30 mol per mol of the lactamide.

15. The process for preparing a lactate according to claim 3 wherein the basic catalyst is selected from the group consisting of an alkaline metal hydroxide, ammonia and an amine.

16. The process for preparing a lactate according to claim 1 wherein step (a) is carried out in the presence of a basic catalyst selected from the group consisting of an alkaline metal, ammonia and an amine; step (b) is carried out in the presence of a catalyst selected from the group consisting of manganese, copper, nickel, manganese oxide, copper oxide and nickel oxide; and step (c) is carried out with a molar feed ratio of the formate to the lactamide of 1 to 10 in the presence of a solvent, said solvent being an alcohol with a molar feed ratio of the alcohol to the lactamide of 1 to 10 and in the presence of a catalyst selected from the group consisting of (i) an alcoholate of an alkali metal selected from the group consisting of lithium, sodium and potassium, wherein said alcoholate is selected from the group consisting of a methylate, an ethylate and a butylate; (ii) an oxide of an alkaline earth metal selected from the group consisting of magnesium oxide, calcium oxide, barium oxide; and (iii) a strongly basic ion exchange resin.

17. The process for preparing a lactate according to claim 16 wherein in step (c), the formate is methyl formate; in step (b), the catalyst is manganese oxide and step (b) is carried out at a temperature of 10° to 150° C. for a reaction time of 0.3 to 6 hours; and step (c) is carried out at a temperature of 20° to 80° C., at a reaction time of 0.5 to 6 hours and the catalyst in step (c) being in an amount of 0.001 to 0.30 mol per mol of the lactamide.

* * * * *